(12) United States Patent
Cho et al.

(10) Patent No.: US 10,272,092 B2
(45) Date of Patent: Apr. 30, 2019

(54) COMPOSITION FOR PREVENTING OR TREATING MUCOSITIS COMPRISING NECROX AS EFFECTIVE INGREDIENT

(71) Applicant: THE CATHOLIC UNIVERSITY OF KOREA INDUSTRY-ACADEMIC COOPERATION FOUNDATION, Seoul (KR)

(72) Inventors: Seok Goo Cho, Seoul (KR); Keon-Il Im, Seoul (KR); Jung Yeon Lim, Seoul (KR); Nayoun Kim, Seoul (KR); Young Sun Nam, Gyeonggi-do (KR); Eun Sol Lee, Gyeonggi-do (KR)

(73) Assignee: The Catholic University of Korea Industry-Academic Cooperation, Seoul (KR)

( * ) Notice: Subject to any disclaimer, the term of this patent is extended or adjusted under 35 U.S.C. 154(b) by 0 days.

(21) Appl. No.: 15/523,197

(22) PCT Filed: Nov. 3, 2015

(86) PCT No.: PCT/KR2015/011691
§ 371 (c)(1),
(2) Date: Apr. 28, 2017

(87) PCT Pub. No.: WO2016/072692
PCT Pub. Date: May 12, 2016

(65) Prior Publication Data
US 2017/0319592 A1 Nov. 9, 2017

(30) Foreign Application Priority Data

Nov. 3, 2014 (KR) .................. 10-2014-0151255
Nov. 2, 2015 (KR) .................. 10-2015-0152916

(51) Int. Cl.
| | | |
|---|---|---|
| *A61K 31/541* | (2006.01) | |
| *A61K 31/54* | (2006.01) | |
| *A23L 33/10* | (2016.01) | |
| *A61K 33/06* | (2006.01) | |
| *A61K 45/06* | (2006.01) | |
| *A23L 33/00* | (2016.01) | |

(52) U.S. Cl.
CPC ............ *A61K 31/541* (2013.01); *A23L 33/10* (2016.08); *A61K 31/54* (2013.01); *A61K 33/06* (2013.01); *A61K 45/06* (2013.01); *A23L 33/00* (2016.08)

(58) Field of Classification Search
CPC .............. A61K 2300/00; A61K 31/727; A61K 31/496; A61K 31/437; A61K 31/44; A61K 31/4439; A61K 31/4545; A61K 31/5025; A61K 31/506; A61K 31/517; A61K 31/519; A61K 31/573; A61K 31/704; A61K 31/706; A61K 31/7068; A61K 45/06; A61K 31/541; A61K 2800/522; A61K 31/404; A61K 31/4184; A61K 31/427; A61K 31/4375; A61K 31/497; A61K 31/54; A61K 33/06; A61K 47/02; A61K 47/40; A61K 47/6951; A61K 8/492; A61K 9/00; A61K 9/0019; A61B 17/06166; A61B 2017/00526; A61B 2017/00893; A61F 2210/0061; A61F 2210/0076; A61F 2240/001; A61F 2240/002; A61F 2250/0067; A61F 2250/0068; A61F 2310/0097; A61F 2/12; A61L 17/005; A61L 17/145; A61L 2300/602; A61L 2430/04; A61L 27/54; A23L 33/00; A23L 33/10; A61Q 19/00

See application file for complete search history.

(56) References Cited

U.S. PATENT DOCUMENTS 5,739,107 A * 4/1998 Cohen .................... A61K 38/17
424/49

FOREIGN PATENT DOCUMENTS

| KR | 1020130038585 A | 4/2013 |
|---|---|---|
| KR | 101304772 B1 | 8/2013 |
| KR | 1020130088720 A | 8/2013 |
| KR | 1020130140402 A | 12/2013 |
| KR | 1020140018698 A | 2/2014 |

OTHER PUBLICATIONS

KR1020130038585A, published Apr. 18, 2013, translation.*
KR1020130088720A, published Aug. 8, 2013, translation.*
PCT Application No. PCT/KR2015/011691, international Search Report dated May 31, 2016, 7 pages.
Choi, et al., Effect of Necrosis Modulator Necrox-7 on Hepatic Ischemia-Reperfusion Injury in Beagle Dogs, Transplantation Proceedings, 42, 3414-3421, (2010).
Kim et al., NecroX as a Novel Class of Mitochondrial Reactive Oxygen Species and ONOO Scavenger, Arch. Pharm. Res., vol. 33, No. 11, 1813-1823, (2010).
Park et al., An Indole Derivative Protects Against Acetaminophen-Induced Liver Injury by Directly Binding to N-Acetyl-P-Benzoquinone Imine in Mice, Antioxidants & Redox Signaling, vol. 18, No. 14, 1713-1722 (2013).

* cited by examiner

*Primary Examiner* — Audrea B Coniglio
(74) *Attorney, Agent, or Firm* — Leydig, Voit & Mayer, Ltd.

(57) ABSTRACT

The present invention relates to a composition for preventing or treating mucositis comprising NecroX. It was found that NecroX has effects of reducing the disease mortality rate by means of radiotherapy or chemotherapy in a NecroX administration group, protecting intestinal functions, inhibiting destruction of intestinal mucous membrane, and proliferating the cells present in intestines. NecroX may be used for a pharmaceutical composition for preventing or treating mucositis, an anti-cancer adjuvant, or a food composition.

8 Claims, 8 Drawing Sheets

COMPOSITION FOR PREVENTING OR TREATING MUCOSITIS COMPRISING NECROX AS EFFECTIVE INGREDIENT

CROSS-REFERENCE TO RELATED APPLICATION

This application claims priority to and the benefit of PCT Application No. PCT/KR2015/011691, filed Nov. 3, 2015, which claims priority to Korean Application No. 10-2015-0152916, filed Nov. 2, 2015 and Korean Application No. 10-2014-0151255, filed Nov. 3, 2014, the disclosure of which is incorporated herein by reference in its entirety.

TECHNICAL FIELD

The present invention relates to a composition for preventing or treating mucositis which includes NecroX as an effective ingredient.

BACKGROUND ART

Mucositis is a side effect of radiotherapy and chemotherapy mainly targeting cancer patients, and refers to a condition in which inflammation occurs in the intramucosal layer lining the mucous membrane or digestive tract. Symptoms of mucositis include thinning of the intramucosal layer due to cell death, peeling thereof and occurrence of inflammation, resulting in ulceration. These lesions are extremely painful and may occur at sites within the digestive tract from the mouth to the anus, including the esophagus, stomach, small intestine, colon, and rectum. The occurrence of mucositis lowers the quality of life of patients. Severe pain in the oral cavity caused by mucositis leads to insufficient nutritional intake and impaired immune functionality. It can even lead to serious conditions that require stopping cancer treatment. However, currently available therapies lack approaches for effectively preventing or treating mucositis.

NecroX is a mitochondria-specific necroptosis inhibitor developed by LG Life Sciences, Ltd, and has received much attention as an innovative material simultaneously exhibiting an effect of inhibiting cell death due to toxins or stress, an effect of enhancing cell viability, and an antioxidant effect. It has been reported that, when human lung fibroblasts (LB-HEL cells) are treated with NecroX after being exposed to low-temperatures for 24 hours, NecroX has an effect of protecting against cell death caused by the low-temperature and an effect of preventing necrocytosis caused by tertbutylhydroperoxide (t-BHP) [Kim et al., Arch Pharm Res. 2010 November; 33(11) 1813-23; Choi et al., Transplant Proc. 2010 November; 42(9) 3414-21]. In particular, it has been reported that NecroX-7 has a protective effect against necrocytosis caused by oxidative stress and acetaminophen and an effect of preventing liver injury caused by carbon tetrachloride in a mouse model, and effectively inhibits liver injury due to ischemic reperfusion [Park et al., Antioxid Redox Signal. 2013 May 10; 18(14) 1713-22].

In addition, NecroX has been proven to also have a cancer metastasis inhibitory effect [Korean Patent Application Publication No. 2013-0088720].

DISCLOSURE

Technical Problem

Therefore, the inventors of the present invention verified a mucosal protective effect, an inhibitory effect with respect to destruction of the oral and intestinal mucosa, and an effect with respect to the proliferation of cells present in the intestines, when a mucositis model induced by radiotherapy or chemotherapy is treated with NecroX, thus completing the present invention.

Aspects of the present invention provide a composition for preventing or treating mucositis, including, as an effective ingredient, NecroX, a pharmaceutically acceptable salt thereof, or an isomer thereof.

Technical Solution

The prevent invention provides a composition for preventing or treating mucositis which includes, as an effective ingredient, NecroX, a pharmaceutically acceptable salt thereof, or an isomer thereof.

The present invention also provides an anticancer adjuvant including, as an effective ingredient, NecroX, a pharmaceutically acceptable salt thereof, or an isomer thereof.

The present invention also provides a food composition for preventing or treating mucositis which includes, as an effective ingredient, NecroX, a pharmaceutically acceptable salt thereof, or an isomer thereof.

Advantageous Effects

According to the present invention, as a result of examining a mucosal protective effect in a mucositis model induced by radiotherapy or chemotherapy according to treatment with NecroX, the mortality rate of the disease induced by radiotherapy or chemotherapy is decreased in a NecroX-administered group and NecroX exhibits effectiveness in alleviating body weight loss. In addition, as a result of examining intestinal functions of the NecroX-administered group, the NecroX-administered group exhibits a stool production rate similar to that of a normal group, which indicates that the intestines are protected, and NecroX suppresses the destruction of the intestinal mucosa by radiation and also contributes to the proliferation rate of cells present in the intestines.

BEST MODE

Figure 1:
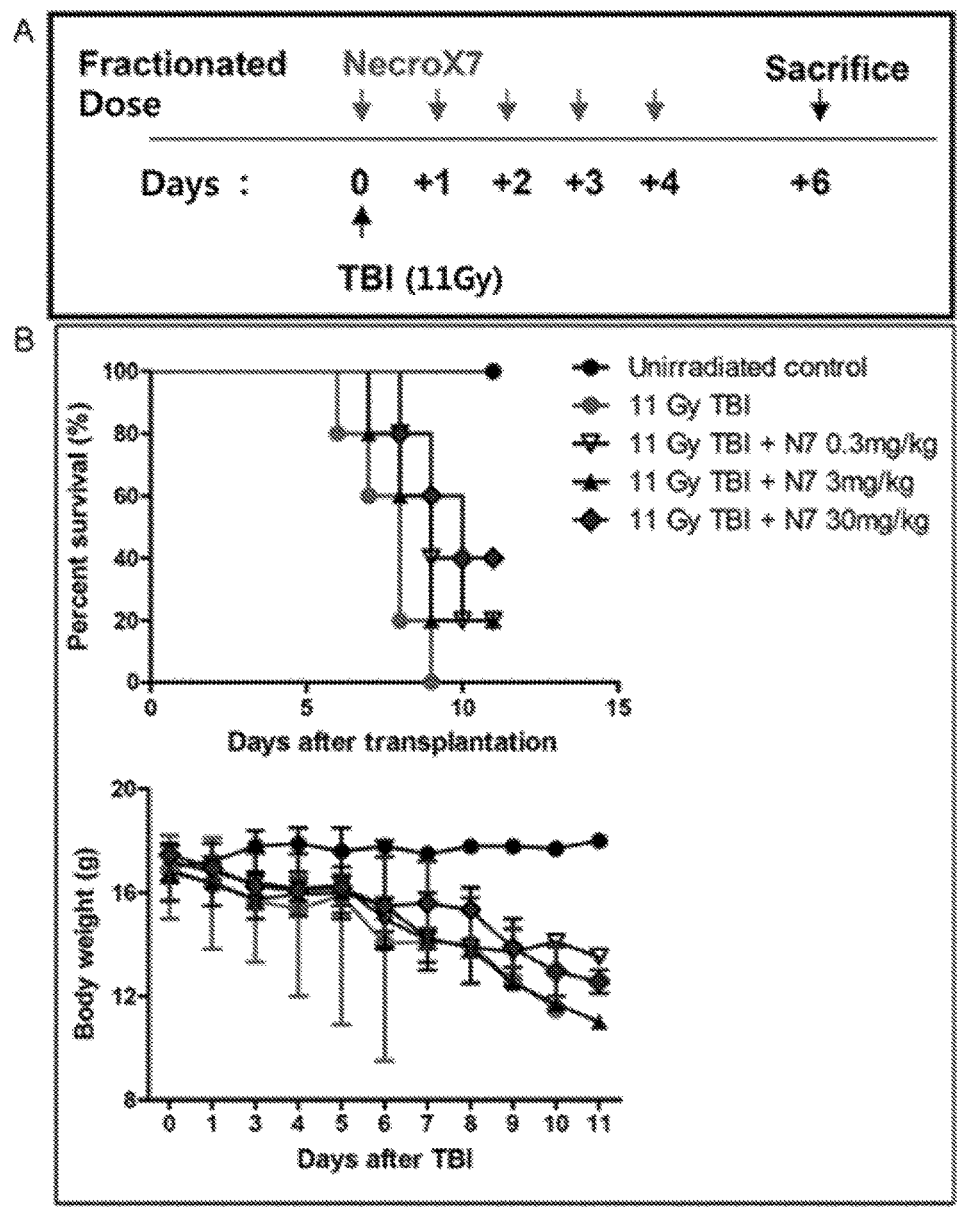
FIG. 1A is a diagram illustrating an experimental design for establishing a radiation-induced mucositis animal model.
FIG. 1B is a graph showing viability and body weight after NecroX-7 was administered to the radiation-induced mucositis animal model.

The present invention relates to a composition for preventing or treating mucositis, including, as an effective ingredient, NecroX, a pharmaceutically acceptable salt thereof, or an isomer thereof.

NecroX is a compound disclosed in Korean Patent Application Publication No. 10-2009-0018593 and is not particularly limited in terms of types thereof, but preferably includes one or more selected from the group consisting of NecroX-1, NecroX-2 ([5-1,1-dioxo-thiomorpholine-4-ylmethyl)-2-phenyl-1H-indole-7-yl]-(1-methanesulfonyl-piperidin-4-yl)-amine), NecroX-5 ([5-(1,1-dioxo-thiomorpholine-4-ylmethyl)-2-phenyl-1H-indole-7-yl]-(tetrahydropyran-4-ylmethyl)-amine), NecroX-7 ((tetrahydropyran-4-yl)-[2-phenyl-5-(1,1-dioxo-thiomorpholine-4-yl)methyl-1H-indole-7-yl]amine), and NecroX-18.

The term "pharmaceutically acceptable salt" as used herein includes pharmaceutically acceptable, anion-containing, nontoxic acid addition salts formed by acids, for example, inorganic acids such as sulfuric acid, hydrochloric acid, nitric acid, phosphoric acid, hydrobromic acid, hydroiodic acid, and the like; organic carboxylic acids such as tartaric acid, formic acid, citric acid, acetic acid, trichloroacetic acid, trifluoroacetic acid, gluconic acid, benzoic acid, lactic acid, fumaric acid, maleic acid, salicylic acid, and the like; sulfonic acids such as methane sulfonic acid, ethane sulfonic acid, benzene sulfonic acid, p-toluene sulfonic acid, naphthalene sulfonic acid, a the like; and the like. In addition, the pharmaceutically acceptable salt includes pharmaceutically acceptable base addition salts, for example, alkali metal or alkali earth metal salts formed by lithium, sodium, potassium, calcium, magnesium, and the like; amino acid salts such as lysine, arginine, guanidine, and the like; organic salts such as dicyclohexylamine, N-methyl-D-glucamine, tris(hydroxymethyl)methylamine, diethanolamine, choline, triethylamine, and the like; and the like. The compound according to the present invention, i.e., (tetrahydropyran-4-yl)-[2-phenyl-5-(1,1-dioxo-thiomorpholine-4-yl)methyl-1H-indole-7-yl]amine, may be converted into a salt thereof using a conventional method known in the art, and the preparation of salts may be easily carried out by one of ordinary skill in the art without further description.

The term "isomer" as used herein refers to compounds or salts thereof having the same chemical or molecular formula but being optically or stereoscopically different. NecroX according to the present invention may have an asymmetric carbon center, and thus may exist as an optical isomer (R or S isomer), a racemate, a mixture of diasteroeomers, an individual diastereomer, or the like, and may also exist as a geometric isomer (trans or cis isomer). All isomers thereof and mixtures thereof are also within the scope of the present invention.

Unless otherwise specified hereinafter, pharmaceutically acceptable salts of NecroX, which is the compound according to the present invention, and/or isomers thereof are all within the scope of the present invention.

In the present invention, a mucosal protective effect of NecroX, with which a mucositis model induced by radiation and/or anticancer treatment was treated, was evaluated. As a result, NecroX decreased the mortality rate of the disease by radiation in a NecroX-administered group and was effective in alleviating body weight loss. In addition, as a result of evaluating intestinal functions, the NecroX-administered group had a stool production rate similar to that of a normal group, which indicates that the intestines were protected, and NecroX inhibited the destruction of the intestinal mucosa by radiation and also contributed to the proliferation rate of cells present in the intestines.

Thus, NecroX of the present invention may treat mucositis induced by radiotherapy or chemotherapy.

The term "mucositis" as used herein includes the concept of thinning and ulceration of the mucous membrane of the gastrointestinal tract (GI) of a subject to be treated, and includes, for example, erythematous red lesions or irregular, concentrated or sporadic ulcerative lesions. For example, erythematous mucositis appears within only 3 days, more generally, 5 days to 7 days after exposure to chemotherapy or radiotherapy, and progresses to ulcerative mucositis within 7 days after the start of chemotherapy and, in some cases, it becomes so severe that medicine treatment must be stopped.

The term "mucositis" as used herein includes alimentary mucositis and vaginal mucositis, including the gastrointestinal tract from mouth to anus as well as oral cavity and oral pharyngeal areas. Alimentary mucositis includes oral mucositis and/or enteritis (inflammation of the intestines, in particular, inflammation of the small intestine), and gastrointestinal mucositis includes esophagitis (inflammation of the esophagus), pharyngitis, stomatitis (inflammation of the stomach), and/or rectitis (inflammation of the rectum).

According to an embodiment of the present invention, a therapeutically effective amount of the compound of the present invention is administered to one or more gastrointestinal sites of a subject with mucositis or having a risk of contracting mucositis.

When body weight is reduced by anticancer therapy (radiotherapy or chemotherapy), the compound of the present invention may be used to alleviate and/or prevent body weight loss to prevent unwanted body weight loss.

Thus, the present invention extends to the prevention of mucositis and/or body weight loss of a subject undergoing radiotherapy and/or chemotherapy.

In the present invention, mucositis and/or body weight loss may occur in a subject exposed to chemical damage, biological damage, radiation, or a mixture thereof, and radiation exposure may result from radiotherapy or the like for anticancer treatment, or may accidentally occur or be caused by a terrorist attack. In addition, a composition, method and use of the present invention may also relate to administration to a subject to prevent, treat or alleviate mucositis and/or body weight loss before or after space travel.

The composition of the present invention may be administered to a subject before damage that may induce or cause the progression of mucositis and/or body weight loss, and, after a subject is damaged, may be administered to the subject before initiation and occurrence of mucositis and/or body weight loss.

The expression "preventing or treating mucositis" as used herein includes inhibition of the development of mucositis or prevention and treatment of mucositis, treatment or prevention of symptoms of patients not having gastrointestinal mucositis but having a risk of developing the same (e.g., cancer patients and other patients previously treated by radiotherapy and/or anticancer therapy, being currently treated, or to be treated), alleviation of aggravation of mucositis due to other cancer treatments, and the like.

Accordingly, the present invention provides a pharmaceutical composition for preventing or treating mucositis, including, as an effective ingredient, NecroX, a pharmaceutically acceptable salt thereof, or an isomer thereof.

A subject to which the pharmaceutical composition is administered is not particularly limited, but may preferably be mammals including livestock, a human, and the like.

The pharmaceutical composition may be administered to a mammal, including a human and the like, to prevent mucositis and also treat mucositis.

The amount of the effective ingredient may range from 0.1 wt % to 99 wt % based on a total weight of the pharmaceutical composition, but the present invention is not limited thereto.

The pharmaceutical composition according to the present invention may include an appropriate carrier, excipient or diluent generally used in the preparation of pharmaceutical compositions, and may be prepared in any formulation generally prepared in the art (e.g., document [Remington' Pharmaceutical Science, latest edition: Mack Publishing Company, Easton Pa.]).

The pharmaceutical composition according to the present invention may be formulated, using a generally used method, in the form of oral formulation such as powder, granules, a tablet, a capsule, a suspension, an emulsion, a syrup, aerosols, or the like; an external application formulation, a suppository, and a sterilized injection solution. The formulation may be prepared using a filler, a thickening agent, a binder, a humectant, a disintegrator, a diluent such as a surfactant, or an excipient, which are generally used.

Examples of solid preparations for oral administration include tablets, pills, powder, granules, capsules, and the like. Such solid preparations are formulated by mixing the compound with at least one excipient, for example, starch, calcium carbonate, sucrose, lactose, gelatin, or the like. In addition to the simple excipient, lubricants such as magnesium stearate or talc are used. Liquid preparations for oral administration include suspensions, liquid solutions, emulsions, syrups, and the like, and may include a commonly used simple diluent such as water or liquid paraffin, and various excipients, for example, humectants, sweetening agents, aromatic agents, preservatives, and the like.

Preparations for parenteral administration include a sterilized aqueous solution, a non-liquid solution, a suspension, an emulsion, a freeze-dried preparation, and a suppository. Non-limiting examples of the non-liquid solution and the suspension include propylene glycol, polyethylene glycol, vegetable oils such as olive oil, and injectable esters such as ethyloleate. Bases for the suppositories may include Witepsol, Macrogol, Tween-61, cacao butter, laurin fat, glycerogelatin, and the like.

The pharmaceutical composition may be administered, via various routes, to mammals such as rats, mice, livestock, humans, and the like. All administration methods may be expected and may, for example, be selected from oral administration, dermal injection, intraperitoneal injection, rectal injection, subcutaneous injection, intravenous injection, intramuscular injection, intrathoracic injection, and the like.

In addition, the composition of the present invention may be used alone or in combination with surgery, radiation treatment, hormone treatment, chemotherapy, a method of using a biological response modifier, or the like, to prevent and/or treat mucositis.

The present invention also provides a method of preventing or treating mucositis, including administering a therapeutically effective amount of NecroX, a pharmaceutically acceptable salt thereof, or an isomer thereof to a subject.

The term "subject" as used herein refers to a mammal that is a subject of treatment, observation, or experimentation, preferably a human.

The term "therapeutically effective amount" as used herein refers to the amount of an effective ingredient or pharmaceutical composition that induces a biological or medical response in a tissue system, animal or human, as contemplated by a researcher, a veterinarian, a doctor, or other clinicians, and includes amounts that induce alleviation of symptoms of treated diseases or disorders. It will be obvious to one of ordinary skill in the art that the therapeutically effective amount and times of administration of the effective ingredient of the present invention may vary according to desired effects. Thus, an optimal dosage to be administered may be easily determined by one of ordinary skill in the art, and may vary according to type of disease, the severity of disease, amounts of the effective ingredient and other ingredients included in the composition, type of formulation, body weight of a patient, age of a patient, gender, body conditions, diet, administration time, administration method, excretion rate, and the like. In the treatment method of the present invention, NecroX of the present invention may be administered to an adult once or several times a day in a dose of about 0.3 mg/kg to about 30 mg/kg, or about 3 mg/kg to about 30 mg/kg.

In the treatment method of the present invention, the composition of the present invention including, as an effective ingredient, NecroX, a pharmaceutically acceptable salt thereof, or an isomer thereof may be administered orally or parenterally (e.g., intravenously, subcutaneously, intraperitoneally, or locally).

The present invention also provides a use of NecroX, a pharmaceutically acceptable salt thereof, or an isomer thereof to prepare a composition for preventing or treating mucositis.

In addition, the pharmaceutical composition according to the present invention may prevent and/or treat mucositis that may occur during anticancer treatment such as radiotherapy or chemotherapy, and thus may also be used as an anticancer adjuvant, in combination with an anticancer drug, As used herein, the anticancer adjuvant may act as an anticancer activity adjuvant that enhances sensitivity to an anticancer drug, prevents and/or treats side effects caused by the anticancer treatment, for example, mucositis, and increases activity by anticancer treatment.

The anticancer drug as used herein is selected from the group consisting of an alkylating agent, an antimetabolite, an antibiotic, a plant alkaloid, a molecular targeting drug, a hormone, a platinum complex, an antisense, an antibody, and RNAi.

Examples of suitable anticancer drugs include: alkylating agents such as cyclophosphamide and busulfan; antimetabolites such as methotrexate, 6-mercaptopurine (6-MP), azathioprine, fluorouracil (5-FU), tegafur, and cytosine arabinoside (ara-C); antibiotics such as bleomycin, mitomycin C, daunorubicin, adriamycin, and actimycin D; plant alkaloids such as vincristine, vinblastine, vindesine, paclitaxel, docetaxel, etoposides, and irinotecan; molecular targeting drugs such as imatinib, gefinitib, elotinib, sorafenib, sunitinib, trastuzumab, rituximab, gemtuzumab-ozogamicin, bevacizumab, and cetuximab; hormones such as prednisolone, diethylstilbestrol, and tamoxifen; platinum complexes such as cisplatin, carbonplatin, and oxaliplatin; antisenses such as bcl-2 antisense (e.g., G3139), hsp27 antisense (e.g., OGX427), XIAP antisense (e.g., AEG35156), PKC-alpha antisense (e.g., LY900003), hypoxia-induced factor antisense (e.g., EZN-2968); antibodies such as a CD20 antibody (e.g., rituximab), Her2 antibody (e.g., trastuzumab), VEGF antibody (e.g., bevacizumab), EGFR antibody (e.g., imab); RNAi such as RNAi targeted ribonucleotide reductase (e.g., CALAA-01). Preferable examples of anticancer drugs include 5-FU, tegafur, and cisplatin.

Examples of suitable chemotherapeutic agents used in combination with the composition of the present invention include mitotic inhibitors such as vinblastine; alkylating agents such as cisplatin, carboplatin, and cyclophosphamide; microtubule assembly inhibitors such as paclitaxel and other taxanes; metabolic antagonists such as 5-fluorouracil, capecitabine, cytosine arabinoside, and hydroxyurea; intercalating antibiotics such as adriamycin and bleomycin; immunostimulants such as trastuzumab; DNA synthesis inhibitors such as gemcitabine; enzymes such as asparaginase; topoisomerase inhibitors such as etoposides; biological response modifiers such as interferon; and anti-hormones such as antiestrogen (e.g., tamoxifen), or antiandrogens (e.g., 4'-cyano-3-(4-fluorophenylsulfonyl)-2-hydroxy-2-methyl-3'-(trifluoromethyl)-propionanilide) and other therapeutic agents and one or more other anticancer substances selected from main substances described in, for example, DeVita, V. T., Jr., Hellmann, S., Rosenberg, S. A.; in: Cancer: Principles & Practice of Oncology, 5th ed., Lippincott-Raven Publishers (1997).

The present invention also provides a method of administering the combined medicine. In an embodiment, the compound of the present invention and a chemotherapeutic agent are provided consecutively, simultaneously, or via different administration routes. In addition, the compound and the chemotherapeutic agent may be in the same form or in different forms, for example, in solid and liquid forms. The method may include simultaneously administering the compound of the present invention and a chemotherapeutic agent. In one embodiment, the compound of the present invention may be consecutively administered to a subject together with a chemotherapeutic agent. In one embodiment, in the case of simultaneous administration, the compound of the present invention may be administered before the chemotherapeutic agent. In another embodiment, the compound of the present invention may be administered after the chemotherapeutic agent. In one embodiment, the chemotherapeutic agent is provided separately from the compound of the present invention.

In one embodiment of the present invention, a chemotherapeutic agent and the compound of the present invention are administered in combination. Administration in combination means that these ingredients are administered together as a composition or as part of the same single dose. The expression "administered in combination" as used herein also means that the ingredient is administered separately but administered as part of a therapeutic or therapeutic program. In one embodiment, the ingredients are simultaneously administered to a subject. However, the ingredients may be administered separately as separate dosages or dosage forms. When the ingredients are administered separately, the combined administration of the ingredients does not impose any limitation on time, frequency, dosage, or the order of administration of the ingredients.

Non-limiting examples of carcinomas of subjects to which the anticancer adjuvant of the present invention is administered include head and neck cancer, non-Hodgkin's lymphoma, leukemia, colon cancer, bladder cancer, ovarian cancer, gastric cancer, lung cancer, prostate cancer, pancreatic cancer, and colorectal cancer.

The present invention also provides a food composition for preventing or alleviating mucositis, including, as an effective ingredient, NecroX, a pharmaceutically acceptable salt thereof, or an isomer thereof.

A subject to which the food composition is applied is not particularly limited, but may preferably be mammals including livestock, a human, and the like.

Non-limiting examples of foods to which the effective ingredient can be added include various foods, beverages, gums, tea, vitamin complexes, and health functional foods.

The amount of NecroX in a food or beverage may range from 0.01 wt % to 50 wt %, and may range from 0.01 g to 50 g based on 100 ml of a health beverage composition, but the present invention is not limited to the above examples.

Other ingredients of the health functional beverage composition of the present invention are not particularly limited so long as the composition incudes the effective ingredient, and the composition may include, as additional ingredients, various flavorings or natural carbohydrates as in general beverages. In addition to the above-described ingredients, the composition of the present invention may include various nutrients, vitamins, minerals (electrolytes), a synthetic and natural flavoring agent, a colorant and an enhancing agent (e.g., cheese, chocolate, and the like), pectic acid or a salt thereof, alginic acid or a salt thereof, organic acid, protective colloids, a thickening agent, a pH adjusting agent, a stabilizer, a preservative, glycerin, alcohol, a carbonating agent used in carbonated beverages, or the like.

The food composition may include animal feed compositions as well as food consumed by humans.

The feed additive may further include a carrier accepted by poultry, livestock, and the like. In the present invention, the feed additive may be added as it is or a carrier, a stabilizer, and the like may be added thereto, and various nutrients such as vitamins, amino acids, minerals, and the like, antioxidants, antibiotics, antibacterial agents, other additives, and the like may be added according to need, and the shape thereof may be in a suitable form such as powder, a granule, a pellet, a suspension, or the like.

The feed additive of the present invention may be supplied alone or in combination with feed to poultry, livestock, and the like.

Mode for Invention

Hereinafter, the present invention will be described in further detail with reference to the following examples, and these examples are not intended to limit the scope of the present invention.

Example 1. Establishment of Mucositis Mouse Model and Therapeutic Effect of NecroX NecroX-7 ((tetrahydropyran-4-yl)-[2-phenyl-5-(1,1-dioxo-thiomorpholine-4-yl)methyl-1H-indole-7-yl]amine) was obtained from LG Life Sciences, Ltd. 7 week- to 9 week-old C57BL/6(H-2k) mice were used as an animal model, and irradiated with 1,100 cGy whole-body radiation to induce damage to the intestinal mucosa, thereby completing the establishment of a mucositis model. Effects of NecroX-7 administered on such a mucositis model were analyzed by comparison in terms of viability, body weight, and intestinal functions.

In the present experiment, a mucositis inhibitory effect of NecroX in the radiation-induced mucositis mouse model was observed.

(A) C57BL/6(H-2k) mice were irradiated with strong radiation 1100 cGy (radiation source: X-ray Mevatron MXE-2) at a dose rate of 1 Gy/min to induce mucositis. NecroX-7 was administered five times at a dose of 0.3 mg/kg or 3 mg/kg or 30 mg/kg and the results were compared. As a result of this experiment, a NecroX-7 treated group exhibited increased viability and inhibited body weight loss compared to a group not treated therewith (see FIG. 1).

Induction of intestinal mucositis by radiation causes side effects such as intestinal hemorrhaging and fecal incontinence. Thus, in the present experiment, a mucositis model was established by irradiating high-dose radiation of 1100 cGy, and NecroX-7 was treated total five times and the NecroX-7 treated group was compared to a group not treated with NecroX-7. A protective effect of NecroX-7 with respect to radiation-induced intestinal mucositis was examined.

Figure 2:
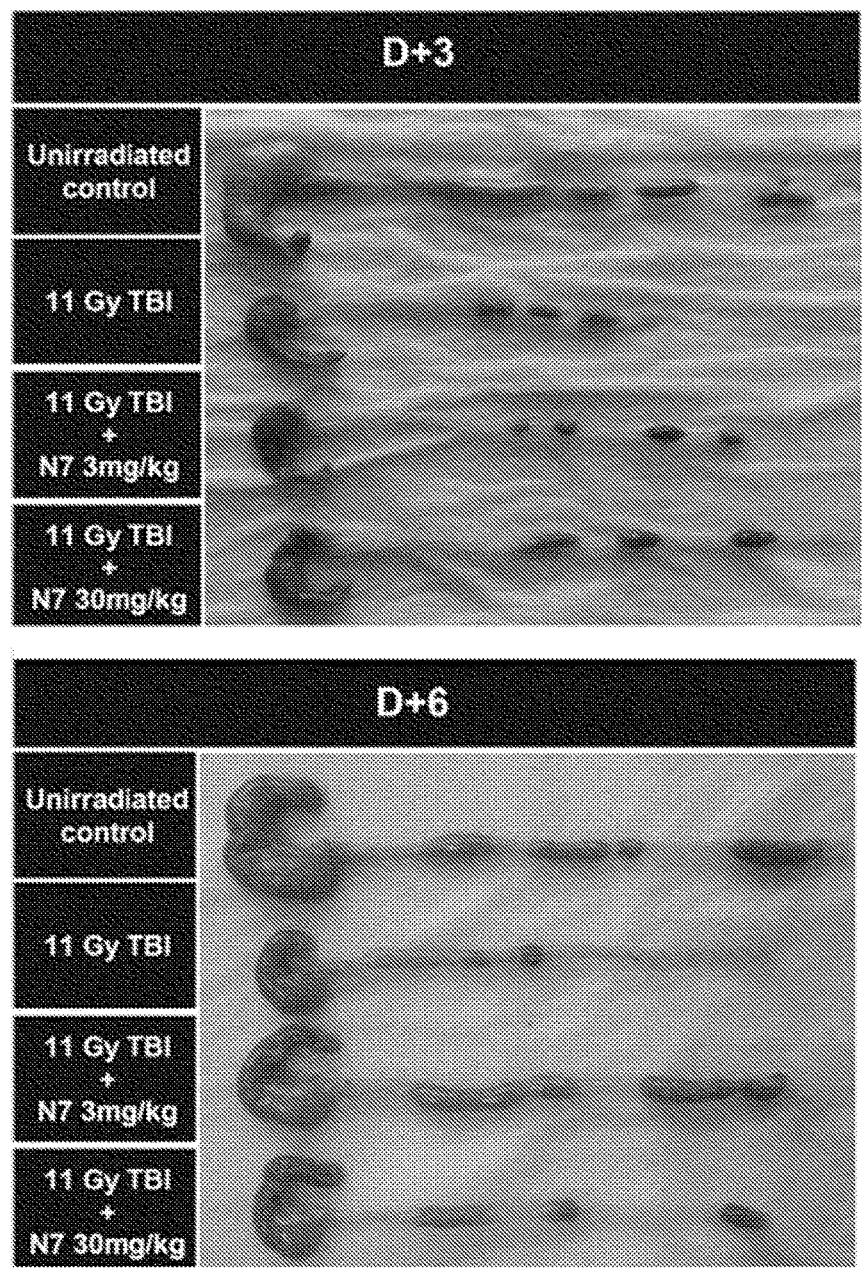
FIG. 2 illustrates images showing intestinal function protective effects after NecroX-7 was administered to a mucositis animal model.

As a result, it was confirmed that, in the group not treated with NecroX-7 and irradiated with radiation (mucositis), the length of the intestines decreased and stool production was significantly reduced. In contrast, it was confirmed that the intestines of the NecroX-7 treated group were protected, similar to the intestines of a normal group (see FIG. 2).

Example 2. Histopathological Examination of Intestinal Function Protective Effect 4 μm continuous sections were obtained from tissue embedded in paraffin and treated with xylene three times to remove paraffin and rinsed stepwise in 95%, 90% and 70% ethanol. After removing endogenous peroxidase from 0.5% hydrogen peroxide, the sections were treated with goat serum for 30 minutes. A primary antibody was diluted in phosphate buffer saline (PBS) containing 3% bovine serum albumin (BSA) according to the manufacturer' instructions and then maintained for 1 hour to induce a reaction therebetween. In this study, after the primary antibody reaction for an expressed protein with respect to genes exhibiting differences in expression, the cells were washed with Tris-buffer saline (TBS) three times, maintained in 5 μg/ml biotinylated anti-mouse/anti-rabbit IgG diluted in 3% BSA for 30 minutes to induce a reaction therebetween, and then washed with TBS three times. The cells were maintained in 3 μg/ml horseradish peroxidase (HRP) streptoavidin for 30 minutes, developed color with DAB and hydrogen peroxide, and then were subjected to contrast staining with Meyer's hematoxylin or 1% methyl green.

Figure 3:
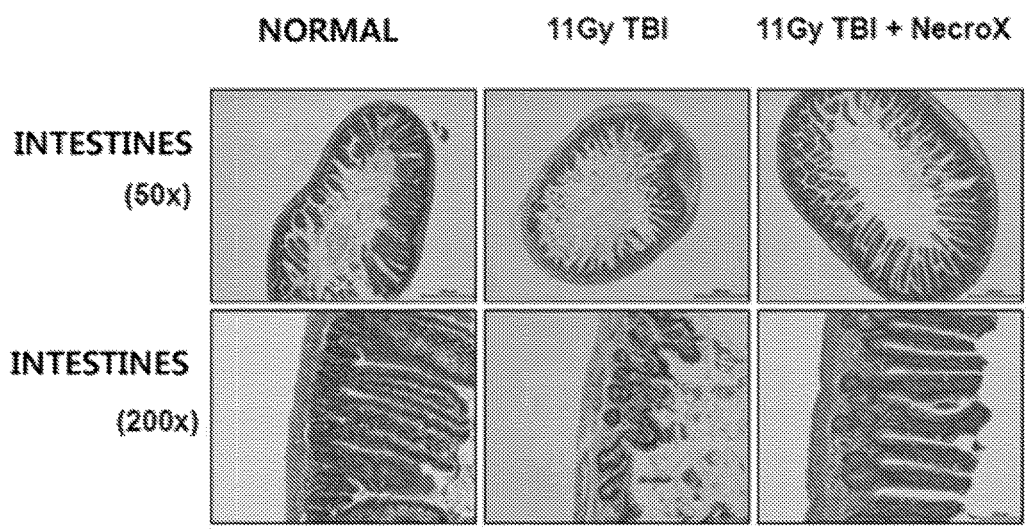
FIG. 3 illustrates hematocylin & eosin (H&E) staining results of an intestinal tissue of each of a mucositis animal model not treated with NecroX-7 and mucositis mice treated with NecroX-7.

Radiation-induced mucositis causes villi destruction in intestinal tissue. In histological views, as a result of H&E staining of intestinal tissue (3 μm sections of paraffin-embedded tissue were attached to slides, followed by deparaffinization in xylene twice for five minutes each, and washed with 100% ethanol twice for five minutes, 90%, 80%, and 70% ethanol for five minutes each, and then running water. The sections were stained with a Meyer's hematoxylin solution for 8 minutes and washed with running water, 70%, 80%, 90%, and 100% ethanol, 100% ethanol for 5 minutes, and then xylene twice for 5 minutes each, followed by sealing and microscopic observation), the mucositis group not treated with NecroX exhibited villi and mucosal destruction of the intestines (As a result of optical microscopic observation after Hematoxylin & Eosin staining, after radiation irradiation, intestinal villi were destroyed, morphological changes such as nuclear atrophy, chromatin condensation, cellular segregation, and the like were observed in cells within crypt sites), while the 30 mg/kg NecroX-7 treated group exhibited aspects similar to normal intestinal tissue (see FIG. 3).

Figure 4:
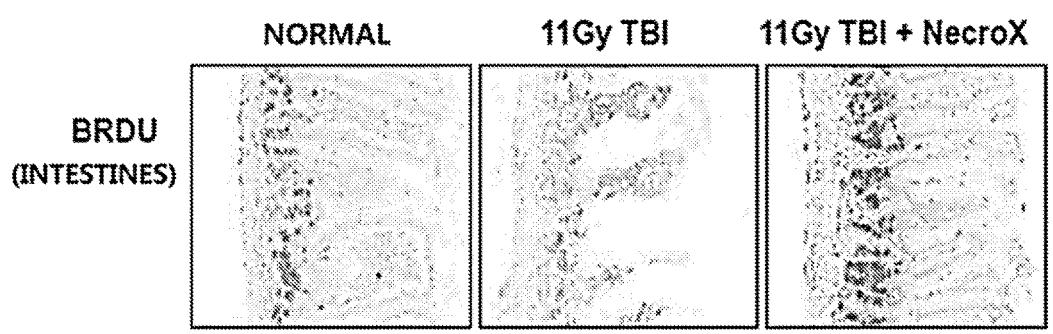
FIG. 4 illustrates images showing cell proliferation (bromodeoxyuridine) results through immunohistochemistry (IHC) analysis of each intestinal tissue taken out of the mucositis animal model not treated with NecroX-7 and the mucositis mice treated with NecroX-7.

Example 3. Effect of NecroX with Respect to Cell Proliferation Inhibition by Radiation Cell proliferation (bromodeoxyuridine) was confirmed by IHC staining. Before obtaining mouse tissues, mice were each injected with 20 g of a BrDU labeling reagent (5-bromo-2'-deoxyuridine and 5-fluoro-2'-deoxyuridine) and intestinal tissue was extracted within 2 hours to prepare paraffin blocks. 4 μm continuous sections were obtained from paraffin-embedded tissue, treated with xylene three times to remove paraffin, and then rinsed stepwise in 95%, 90% and 70% ethanol. After removing endogenous peroxidase from 0.3% hydrogen peroxide, the sections were treated with goat serum for 30 minutes. A primary antibody was diluted in PBS containing 3% BSA according to the manufacturer's instructions and then maintained for 1 hour to induce a reaction therebetween. In this study, after the primary antibody reaction for an expressed protein with respect to genes exhibiting differences in expression, the cells were washed with TBS three times, maintained in 5 μg/ml biotinylated anti-mouse/anti-rabbit IgG diluted in 3% BSA for 30 minutes to induce a reaction therebetween, and then washed with TBS three times. The cells were maintained in 3 μg/ml HRP streptoavidin for 30 minutes, developed color with DAB and hydrogen peroxide, and then were subjected to contrast staining with Mayer's hematoxylin or 1% methyl green. As a result, it was confirmed that, unlike a control, vigorous cell proliferation was observed in the 30 mg/kg NecroX-7 treated group (see FIG. 4).

Example 4. Effect of NecroX on Normal Cells and Tumor Cells by Radiation In Vivo Mucositis is a general side effect caused by radiation or chemotherapy for tumor treatment. Thus, to confirm the efficacy of a mucositis therapeutic agent, an effect thereof on tumor proliferation should be evaluated. Normal cells and tumor cells were irradiated with 800 cGy radiation, treated with NecroX-7 according to doses, and inoculated on a 96-well plate, incubated at 37□ and 5% $CO_2$ for 3 days, and then cell proliferation was confirmed by MTT assay. After incubation for 3 days, an MTT solution was added thereto and a reaction was allowed to occur therein for 3 hours, and the absorbance thereof was measured at 540 nM.

Figure 5:
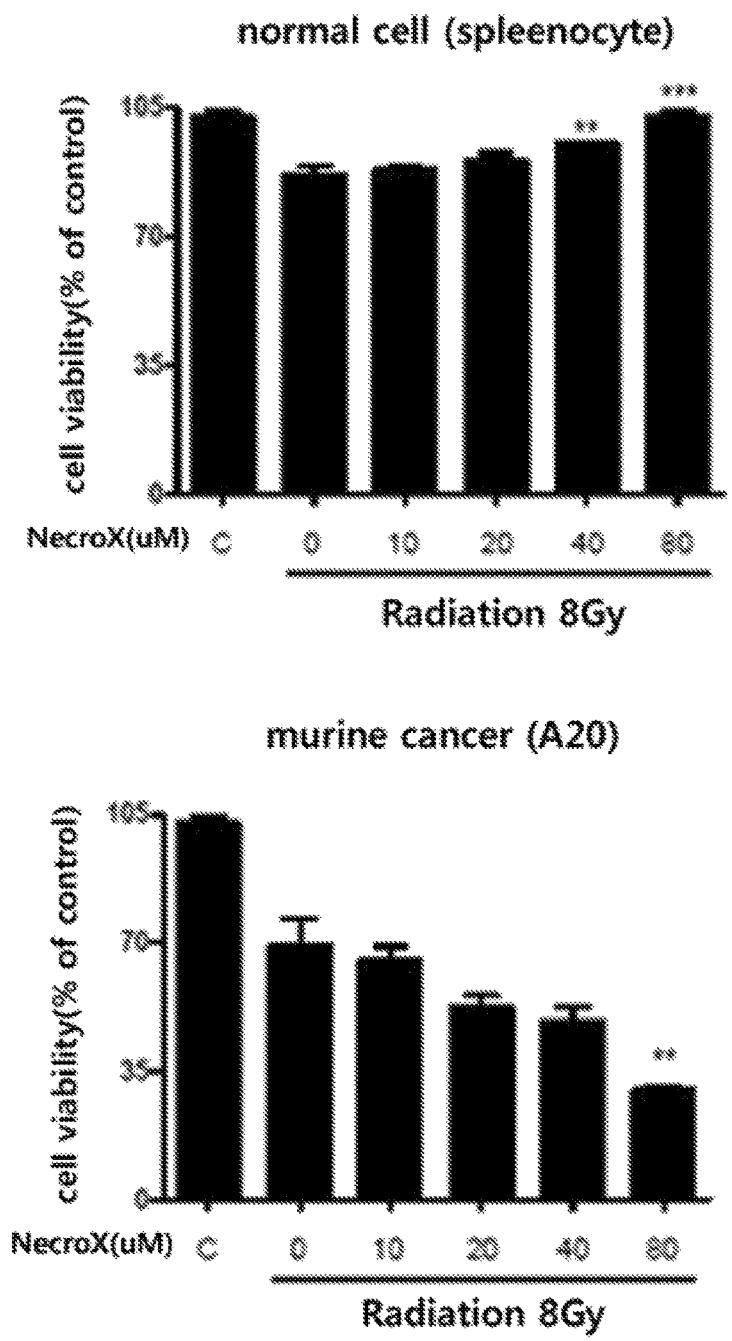
FIG. 5 is a graph showing effects of NecroX-7 on normal cells and cancer cells by radiation.

As a result, it was confirmed that, when NecroX-7 was treated, proliferation of tumor cells was suppressed or decreased in most cancer cell lines, while radiation-induced cell death was prevented in the normal cells (see FIG. 5).

Example 5. Oxidative Stress Regulation in Mitochondria by NecroX-7

Reactive oxygen species (ROS) are generally produced by incomplete combustion of oxygen during intracellular mitochondrial respiration processes, and ROS are greatly increased by radiotherapy or chemotherapy. Thus, the researchers of the present invention verified an effect of NecroX-7 on ROS increased by radiotherapy in intestinal epithelial cells (IEC-6).

To examine an effect of NecroX-7 on IEC-6 cell proliferation ability in normal environments, IEC-6 cells were treated with NecroX-7 at each concentration (5 μM, 10 μM, 20 μM, and 40 μM) for 30 minutes, the media were replaced and, after 2 days, the viability of the IEC-6 cells was measured by MTS (3-(4,5-dimethylthiazol-2-yl)-5-(3-carboxymethoxyphenyl)-2-(4-sulfophenyl)-2H-tetrazolium) assay. There was nearly no effect on cell proliferation according to the concentration of NecroX-7.

Figure 6:
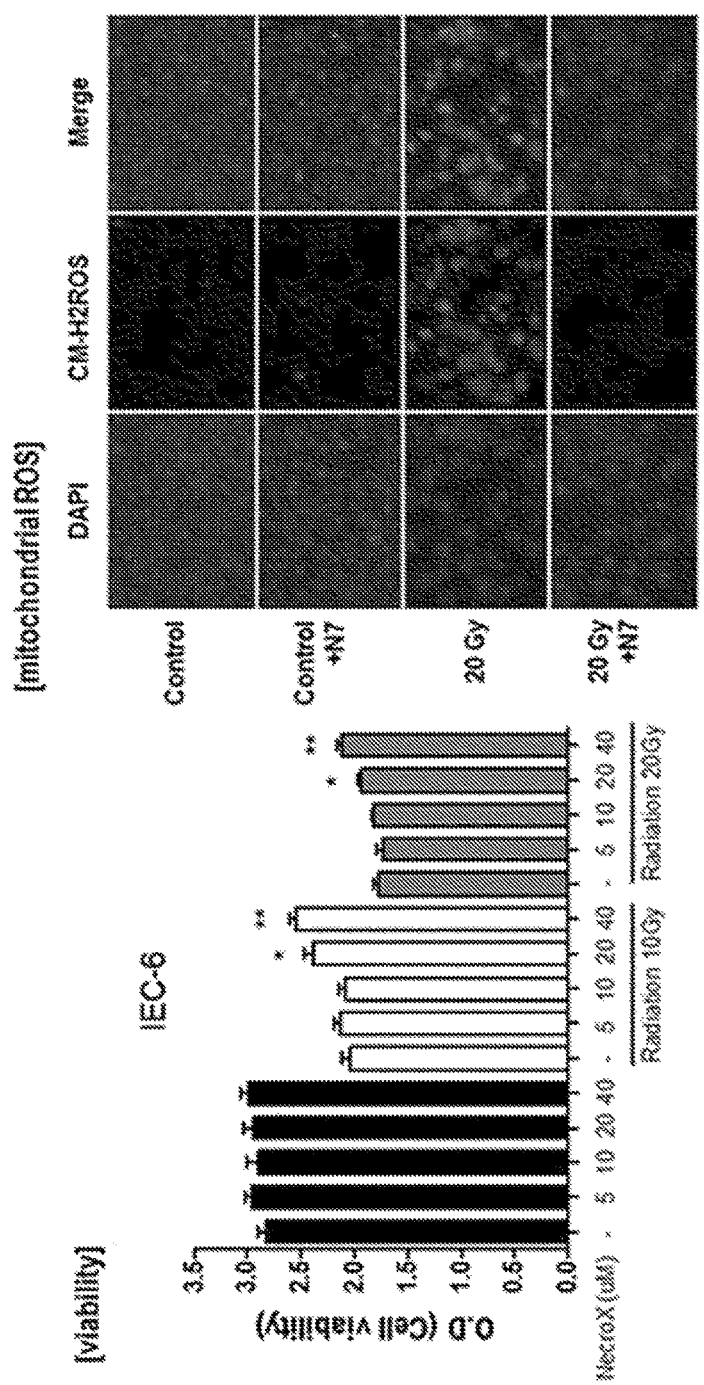
FIG. 6 illustrates measurement results of reactive oxygen species in mitochondria through MTS assay and CM-H2ROS staining to examine an effect of NecroX-7 on cell proliferation ability after radiation

To investigate an effect of NecroX-7 on cell proliferation ability after irradiation, the IEC-6 cells were treated with NecroX-7, for 30 minutes, according to concentration, the media were replaced, and then MTS assay was performed thereon 2 days after radiation irradiation. As a result of MTS assay, the number of live cells was significantly increased at 20 μM and 40 μM NecroX-7. As a result of measuring mitochondrial ROS through CM-H2ROS staining, it was confirmed that NecroX-7 significantly suppressed mitochondrial ROS increased by radiation (see FIG. 6).

Example 6. Establishment of Mucositis Mouse Model by Anticancer Therapy and Therapeutic Effect of NecroX 7 week- to 9 week-old C57BL/6(H-2k) mice were used as an animal model, and injected intraperitoneally with 50 mg/kg of 5-fluorouracil (5-FU) every day for 5 days to induce oral and intestinal mucosal damage, thereby completing the establishment of a mucositis model. Effects of NecroX-7 administered on such a mucositis model were analyzed by comparison in terms of viability, body weight, and intestinal functions.

In the present experiment, a mucositis inhibitory effect of NecroX in the anticancer drug-induced mucositis mouse model was observed.

Figure 7:
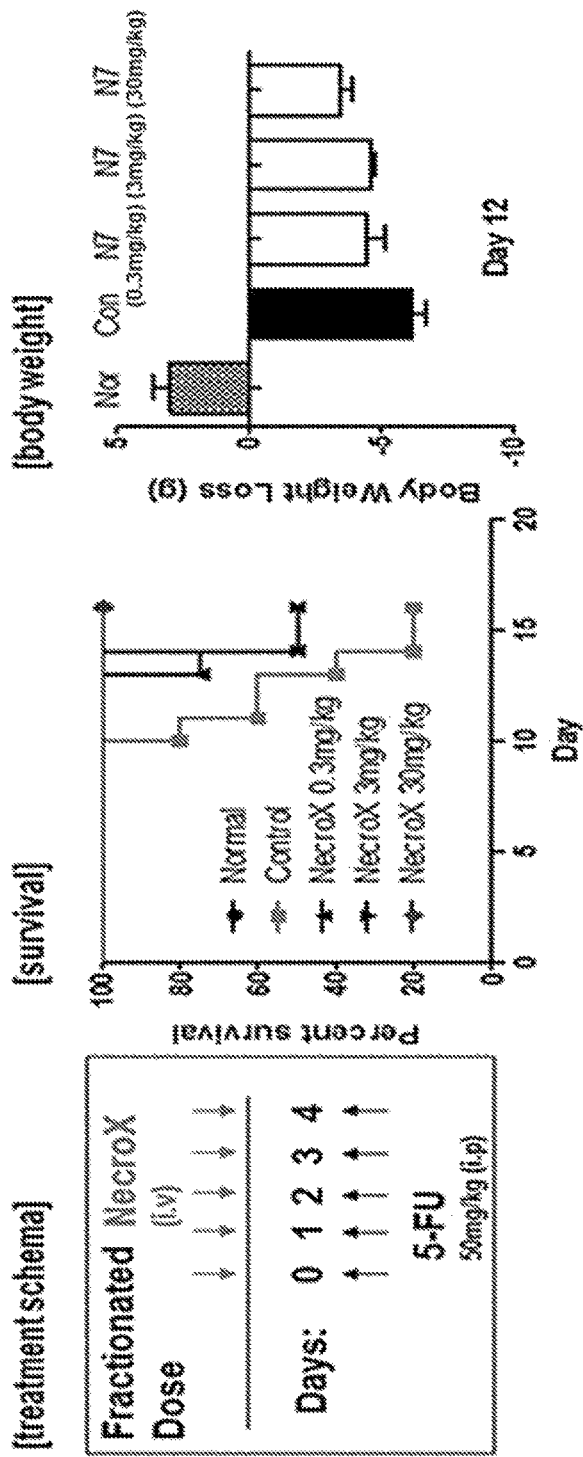
FIG. 7 illustrates a diagram illustrating an experimental design for establishing an anticancer agent-induced mucositis animal model and graphs showing survival rates and body weights after NecroX-7 was administered to the anticancer agent-induced mucositis animal model.

To induce oral and intestinal mucositis, the C57BL/6(H-2k) mice were intraperitoneally injected with 50 mg/kg of 5-FU five times. NecroX-7 was administered intravenously five times at a dose of 0.3 mg/kg or 3 mg/kg or 30 mg/kg and the results were compared. As a result of this experiment, a NecroX-7 treated group exhibited increased viability and suppressed body weight loss compared to a group not treated therewith (see FIG. 7).

Example 7. Histological Examination of Oral and Intestinal Protective Effects

4 μm continuous sections were obtained from tissue embedded in paraffin and treated with xylene three times to remove paraffin and rinsed stepwise in 95%, 90% and 70% ethanol. After removing endogenous peroxidase from 0.5% hydrogen peroxide, the sections were treated with goat serum for 30 minutes. A primary antibody was diluted in PBS containing 3% BSA according to the manufacturer's instructions and then maintained for 1 hour to induce a reaction therebetween. In this study, after the primary antibody reaction for an expressed protein with respect to genes exhibiting differences in expression, the cells were washed with TBS three times, maintained in 5 μg/ml biotinylated anti-mouse/anti-rabbit IgG diluted in 3% BSA for 30 minutes to induce a reaction therebetween, and then washed with TBS three times. The cells were maintained in 3 μg/ml HRP streptoavidin for 30 minutes, developed color with DAB and hydrogen peroxide, and then were subjected to contrast staining with Meyer's hematoxylin or 1% methyl green.

Figure 8:
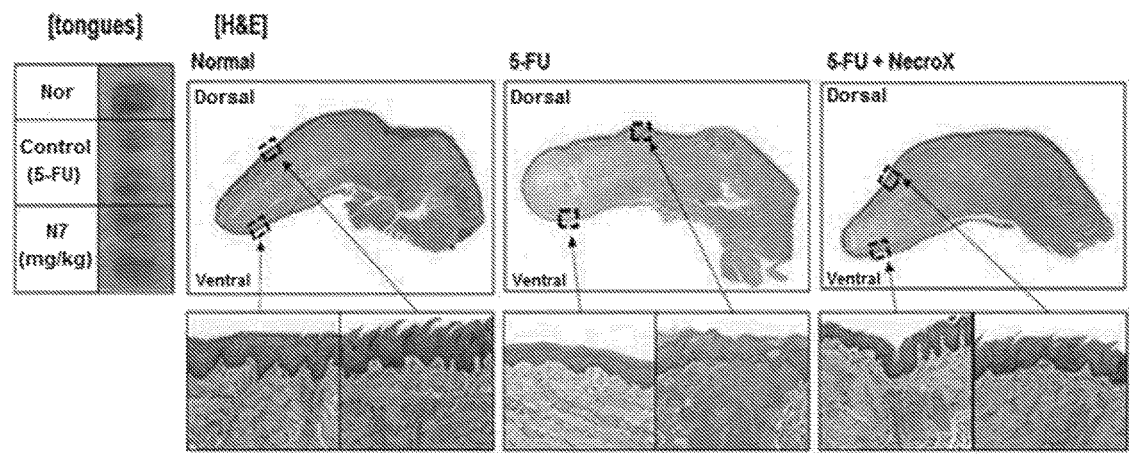
FIG. 8 illustrates H&E staining results of a tongue tissue of each of a mucositis animal model not treated with NecroX-7 and mucositis mice treated with NecroX-7.
Figure 9:
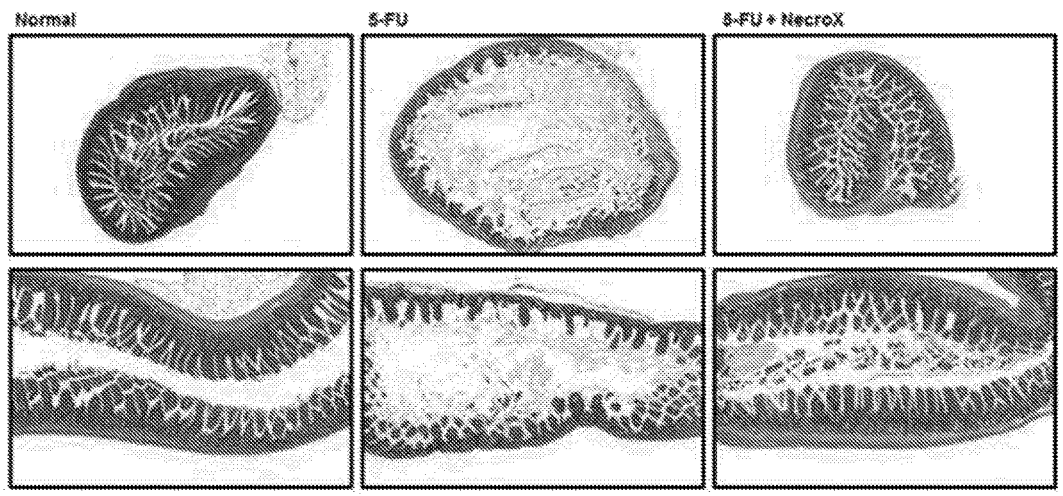
FIG. 9 illustrates H&E staining results of an intestinal tissue of each of the mucositis animal model not treated with NecroX-7 and the mucositis mice treated with NecroX-7.

Anticancer drug-induced mucositis atrophies the epidermal layer of the tongue and oral mucosa and causes the infiltration of inflammatory cells and necrotic cells. In addition, the mucositis causes intestinal hemorrhaging and villi destruction in intestinal tissues. Even in histological views, as a result of H&E staining of the tongue and intestinal tissues (3 μm sections of paraffin-embedded tissues were attached to slides, followed by deparaffinization in xylene twice for five minutes each, and washed with 100% ethanol twice for five minutes, 90%, 80%, and 70% ethanol for five minutes each, and then running water. The sections were stained with a Meyer's hematoxylin solution for 8 minutes and washed with running water, 70%, 80%, 90%, and 100% ethanol, 100% ethanol for 5 minutes, and then xylene twice for 5 minutes each, followed by sealing and microscopic observation), the epidermal layers of the tongue and oral mucosa were atrophied and the infiltration of inflammatory cells and necrotic cells occurred in the mucositis group not treated with NecroX-7, while aspects similar to normal tissues were observed in the group treated with 30 mg/kg of NecroX-7. In addition, intestinal villi and mucosal destruction was observed in the mucositis group not treated with NecroX-7, while aspects similar to normal tongue and intestinal tissues were observed in the NecroX-7-treated group (see FIGS. 8 and 9).

Example 8. Confirmation of Combined Administration Effect of NecroX-7 and Chemotherapeutic Agent Human tumor cells were treated with NecroX-7 at each concentration ((5 μM, 10 μM, 20 μM, and 40 μM) for 30 minutes, the media were replaced by media with or without 5-FU, which is a chemotherapeutic agent, the cells were loaded on a 96-well plate and, after 3 days, the viability of the cells was measured by MTS assay.

Figure 10:
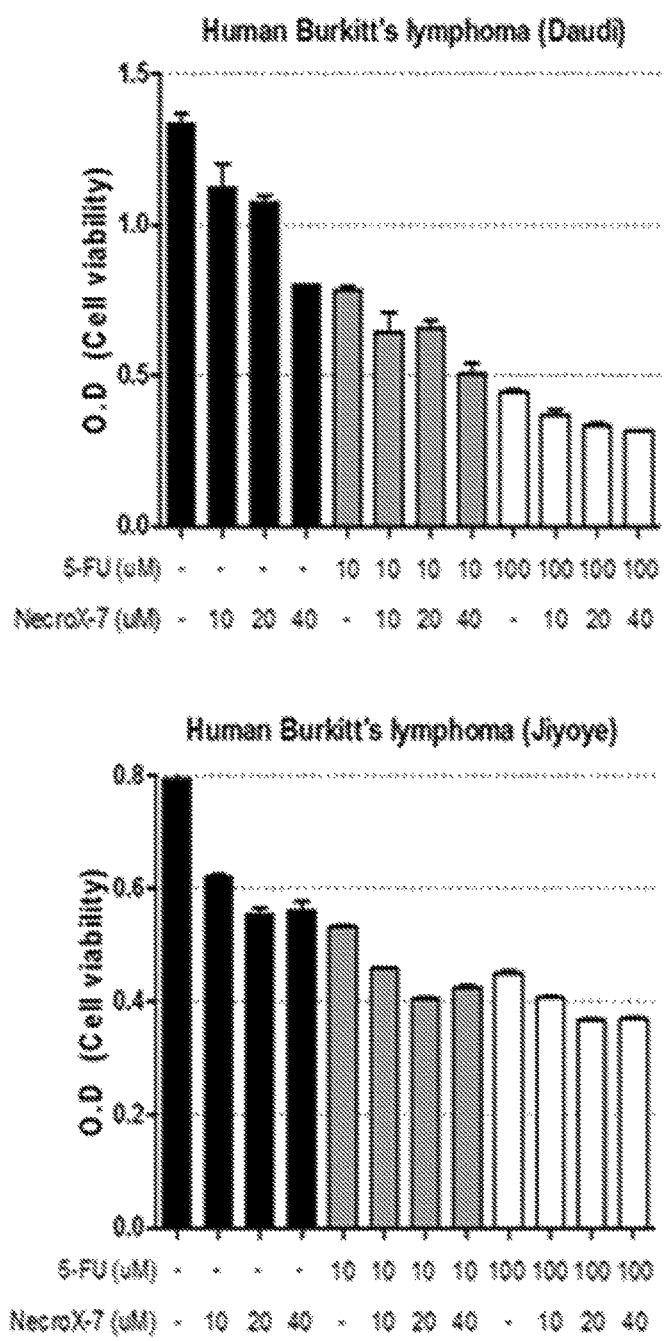
FIG. 10 illustrates analysis results of the viability of tumor cells when treated with NecroX-7 alone according to concentration, treated with 5-fluorouracil (FU) alone as an anticancer agent, and treated with 5-FU and NecroX-7 in combination, to exhibit an effect of NecroX as an anticancer adjuvant on human tumor cells.

As a result, as illustrated in FIG. 10, the human tumor cells treated with NecroX-7 alone exhibited an anticancer effect in a concentration-dependent manner. In addition, tumor cell lines treated with NecroX-7 and 5-FU in combination exhibited a higher cell killing effect than that of tumor cell lines treated with 5-FU alone.

The invention claimed is:

1. A method of preventing or treating mucositis induced by radiotherapy or chemotherapy, comprising administering a therapeutically effective amount of NecroX-7, a pharmaceutically acceptable salt thereof, or an isomer thereof to a subject, in combination with said radiotherapy or chemotherapy.

2. The method of claim 1, wherein the mucositis is induced by radiotherapy.

3. The method of claim 1, wherein the mucositis is induced by chemotherapy.

4. The method of claim 1, wherein the method comprises preventing mucositis induced by radiotherapy or chemotherapy comprising prophylactic administration of NecroX-7.

5. The method of claim 1, wherein the NecroX-7 is administered within 7 days of the radiotherapy or chemotherapy.

6. The method of claim 1, wherein the NecroX-7 is administered intravenously.

7. The method of claim 1, wherein the mucositis is alimentary mucositis.

8. The method of claim 1, wherein the NecroX-7 is administered to one or more alimentary sites.

\* \* \* \* \*